(12) United States Patent
Chen et al.

(10) Patent No.: US 10,101,292 B2
(45) Date of Patent: Oct. 16, 2018

(54) MEMS HUMIDITY SENSOR AND METHOD OF MANUFACTURING THE SAME

(71) Applicant: TAIWAN SEMICONDUCTOR MANUFACTURING CO., LTD., Hsinchu (TW)

(72) Inventors: Tung-Tsun Chen, Hsinchu (TW); Chia-Hua Chu, Hsinchu County (TW); Jui-Cheng Huang, Hsinchu (TW); Chun-Wen Cheng, Hsinchu County (TW); Cheng-Hsiang Hsieh, Taipei (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 157 days.

(21) Appl. No.: 15/053,906

(22) Filed: Feb. 25, 2016

(65) Prior Publication Data

US 2017/0248536 A1   Aug. 31, 2017

(51) Int. Cl.
*G01N 19/00* (2006.01)
*G01N 27/22* (2006.01)

(52) U.S. Cl.
CPC ......... *G01N 27/223* (2013.01); *G01N 27/226* (2013.01)

(58) Field of Classification Search
CPC .......................... G01N 27/223; G01N 27/226
USPC ...................................................... 73/335.04
See application file for complete search history.

(56) References Cited

U.S. PATENT DOCUMENTS

2004/0154417 A1* 8/2004 Renken ............. H01L 21/67253
                                                         73/866.1
2015/0068302 A1* 3/2015 Koo ..................... G01N 27/223
                                                         73/335.04

OTHER PUBLICATIONS

Y. Y. Qiu et al., "A CMOS humidity sensor with on-chip calibration", Elsevier, Sensors and Actuators A 92 (2001) 80-87.
Laconte, J. et al., "High-Sensitivity Capacitive Humidity Sensor Using 3-Layer Patterned Polyimide Sensing Film", Sensors, 2003. Proceedings of IEEE (vol. 1), pp. 372-377.

* cited by examiner

*Primary Examiner* — John Fitzgerald
*Assistant Examiner* — Rodney T Frank
(74) *Attorney, Agent, or Firm* — Maschoff Brennan

(57) ABSTRACT

A micro-electro mechanical system (MEMS) humidity sensor includes a first substrate, a second substrate and a sensing structure. The second substrate is substantially parallel to the first substrate. The sensing structure is between the first substrate and the second substrate, and bonded to a portion of the first substrate and a portion of the second substrate, in which the second substrate includes a conductive layer facing the sensing structure, and a first space between the first substrate and the sensing structure is communicated with or isolated from outside, and a second space between the conductive layer and the sensing structure is communicated with an atmosphere, and the sensing structure, the second space and the conductive layer constitute a capacitor configured to measure permittivity of the atmosphere, and humidity of the atmosphere is derived from the permittivity of the atmosphere, pressure of the atmosphere and temperature.

20 Claims, 4 Drawing Sheets

MEMS HUMIDITY SENSOR AND METHOD OF MANUFACTURING THE SAME

BACKGROUND

Humidity sensors are widely used in various fields to measure an amount of water vapor present in the air of a particular environment. However, humidity measured using the humidity sensors is generally derived from fringing capacitance, which is small and thus test sensitivity is too low.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
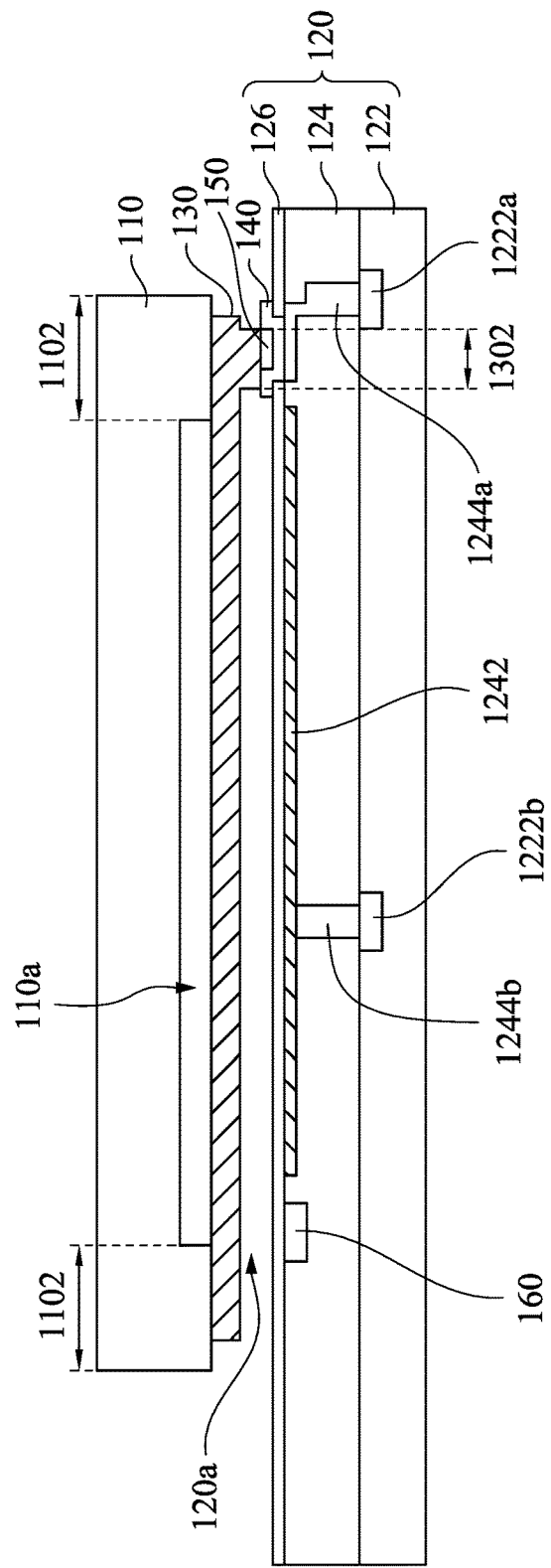
FIG. 1 is a cross-sectional view of a micro-electro mechanical system (MEMS) humidity sensor in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

As mentioned above, humidity measured using the humidity sensors is generally derived from fringing capacitance, which is small and thus test sensitivity is too low. Accordingly, the present disclosure provides a micro-electro mechanical system (MEMS) humidity sensor, in which humidity is derived from parallel plate capacitance, such that the MEMS humidity sensor has higher test sensitivity. The MEMS humidity sensor may measure on-chip pressure and/or temperature to improve accuracy of humidity. In addition, a polyimide film may be integrated with the MEMS humidity sensor to further increase test sensitivity. Embodiments of the MEMS humidity sensor will be described in detail below.

FIG. 1 is a cross-sectional view of a MEMS humidity sensor in accordance with some embodiments of the present disclosure. The MEMS humidity sensor includes a first substrate 110, a second substrate 120 and a sensing structure 130.

The second substrate 120 is substantially parallel to the first substrate 110. The term "substantially parallel" refers to the two elongated members being parallel or almost parallel. In some embodiments, each of the first substrate 110 and the second substrate 120 includes a bulk substrate, such as silicon substrate or a non-silicon substrate. In some embodiments, the first substrate 110 or the second substrate 120 includes an elementary semiconductor including silicon or germanium in crystal, polycrystalline, and/or an amorphous structure; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; any other suitable material; and/or combinations thereof. In some embodiments, the first substrate 110 has a planar dimension (in top view) smaller than or equal to a planar dimension (in top view) of the second substrate 120.

In some embodiments, the first substrate 110 is a MEMS substrate. In some embodiments, the MEMS substrate includes a bulk substrate (e.g., silicon substrate) and an epitaxial layer thereover. In some embodiments, the MEMS substrate includes a buried oxide (BOX) layer. In some embodiments, the MEMS substrate includes metal, such as aluminum, copper, titanium, tantalum, tungsten, molybdenum, tantalum nitride (TaN), nickel silicide, cobalt silicide, titanium nitride (TiN), tungsten nitride (WN), titanium aluminum (TiAl), titanium aluminum nitride (TiAlN), tantalum carbon nitride (TaCN), tantalum carbon (TaC), tantalum silicon nitride (TaSiN), metal alloys, any other suitable material or a combination thereof. Exemplary metal structures within the MEMS substrate include metal traces, metal contacts and metal layers.

In some embodiments, the first substrate 110 includes a first protruding peripheral portion 1102. In some embodiments, the first protruding peripheral portion 1102 is open shaped (e.g., U shaped) or enclosed shaped (e.g., rectangular or circular shaped) in top view.

In some embodiments, the second substrate 120 includes a bulk substrate 122 (e.g., silicon substrate). In some embodiments, the second substrate 120 includes passive components such as resistors, capacitors, inductors, and/or fuses; active components, such as P-channel field effect transistors (PFETs), N-channel field effect transistors (NFETs), metal-oxide-semiconductor field effect transistors (MOSFETs), complementary metal-oxide-semiconductor transistors (CMOSs), high voltage transistors, and/or high frequency transistors; other suitable components; and/or combinations thereof. In some embodiments, the second substrate 120 includes a first transistor 1222a and a second transistor 1222b at a top of the bulk substrate 122. In some embodiments, the first transistor 1222a and the second transistor 1222b are CMOS transistors, such as PMOS transistors and/or NMOS transistors.

In some embodiments, the second substrate 120 includes integrated circuits, such as memory cells, analog circuits, logic circuits and/or mixed-signal circuits. In some embodiments, the second substrate 120 includes an interconnect and interlayer dielectric (ILD) layer 124. In some embodiments, the interconnect and ILD layer 124 includes interconnect (e.g., metal lines and vias) associated with passive components, active components, other suitable components or a combination thereof. In some embodiments, the interconnect and ILD layer 124 includes ILD, which is made of silicon oxide, silicon nitride, silicon oxynitride, any other suitable material or a combination thereof.

The second substrate 120 includes a conductive layer 1242 facing the sensing structure 130. In some embodiments, the conductive layer 1242 is at a top of the interconnect and ILD layer 124. In some embodiments, the conductive layer 1242 is substantially parallel to the sensing structure 130. In some embodiments, the conductive layer 1242 is made of metal or a metal compound, such as Mo, Cr, Al, Nd, Ti, Cu, Ag, Au, Zn, In, Ga, Pt, Ag, Au, any other suitable material or a combination thereof. In some embodiments, the sensing structure 130, the conductive layer 1242 and a second space 120a therebetween constitute a capacitor.

In other embodiments, a conductive layer (not shown) is over the second substrate 120, and the sensing structure 130, the conductive layer (not shown) and a second space 120a therebetween constitute a capacitor. In other words, the conductive layer (not shown) over the second substrate 120 can replace the conductive layer 1242 of FIG. 1. In other embodiments, the conductive layer (not shown) is over the interconnect and ILD layer 124. In other embodiments, the conductive layer (not shown) is made of inert metal, inert metal alloy, any other suitable material or a combination thereof.

In some embodiments, the second substrate 120 further includes an insulating layer 126 over the conductive layer 1242. In some embodiments, the insulating layer 126 is made of silicon oxide, silicon nitride, silicon oxynitride, any other suitable material or a combination thereof. In some embodiments, the insulating layer 126 is configured to prevent the conductive layer 1242 from corrosion.

In some embodiments, the second substrate 120 includes a first sensing circuit 1244a and a second sensing circuit 1244b in the interconnect and ILD layer 124. In some embodiments, the first sensing circuit 1244a and the second sensing circuit 1244b are respectively coupled to the sensing structure 130 and the conductive layer 1242. In some embodiments, the first sensing circuit 1244a and the second sensing circuit 1244b are respectively coupled to the first transistor 1222a and the second transistor 1222b. Therefore, potential of the sensing structure 130 can be measured through the first sensing circuit 1244a and the first transistor 1222a, and potential of the conductive layer 1242 can be measured through the second sensing circuit 1244b and the second transistor 1222b.

The sensing structure 130 is between the first substrate 110 and the second substrate 120, and bonded to a portion of the first substrate 110 and a portion of the second substrate 120. In some embodiments, the sensing structure 130 is made of a conductive material, such as silicon, metal or a combination thereof. In some embodiments, the sensing structure 130 includes silicon and dopants. In some embodiments, the sensing structure 130 is made of hard conductive material, such as silicon.

In some embodiments, the sensing structure 130 includes a second protruding peripheral portion 1302 bonded to the second substrate 120. In some embodiments, the second protruding peripheral portion 1302 is open shaped (e.g., U shaped) in top view. In some embodiments, the first protruding peripheral portion 1102 of the first substrate 110 is substantially aligned with the second protruding peripheral portion 1302 of the sensing structure 130. In some embodiments, the first protruding peripheral portion 1102 has an upper surface (not marked) greater than or equal to an upper surface (not marked) of the second protruding peripheral portion 1302.

In some embodiments, the MEMS humidity sensor includes a first bonding pad 140 and a second bonding pad 150. In some embodiments, the first bonding pad 140 and the second bonding pad 150 are made of metal, alloy, semiconductor material or a combination thereof. In some embodiments, the first bonding pad 140 is over the bonded portion of the second substrate 120. In some embodiments, the first bonding pad 140 is coupled or directly connected to the first sensing circuit 1244a. In some embodiments, the second bonding pad 150 is between the sensing structure 130 and the first bonding pad 140. In some embodiments, the second bonding pad 150 is coupled or directly connected to the sensing structure 130. In some embodiments, the first sensing circuit 1244a is coupled to the sensing structure 130 through the first bonding pad 140 and the second bonding pad 150. In some embodiments, the second bonding pad 150 is over the second protruding peripheral portion 1302. In some embodiments, the first bonding pad 140 has a concave portion (not marked) substantially aligned with a convex portion (not marked) of the second bonding pad 150. In some embodiments, the first bonding pad 140 is bonded to the second bonding pad 150 by eutectic bonding, diffusion bonding or any other suitable bonding type. In some embodiments, the eutectic bonding is Ge/Al, Ge/Au or Si/Au. In some embodiments, the diffusion bonding is Si/Al or Si/Ti.

In some embodiments, a first space 110a formed between the first substrate 110 and the sensing structure 130 is communicated with or isolated from outside; that is, the first space 110a is an open space or an enclosed space. In some embodiments, the first space 110a is vacuum or accommodates atmosphere with known pressure. In other embodiments, a first substrate includes a through hole (not shown) through the first substrate, and a first space is communicated with outside through the through hole.

In some embodiments, the second space 120a formed between the conductive layer 1242 and the sensing structure 130 is communicated with an atmosphere; that is, the second space 120a is an open space. The sensing structure 130, the second space 120a and the conductive layer 1242 constitute the capacitor configured to measure permittivity of the atmosphere, and humidity of the atmosphere is derived from the permittivity of the atmosphere, pressure of the atmosphere and temperature of the atmosphere.

In some embodiments, humidity of the atmosphere is calculated by the formula of $\varepsilon = 1 + a/T[P + (b \times Ps \times H/T)]10^{-6}$, in which $\varepsilon$ is the permittivity of the atmosphere ($\varepsilon = C \times d/A$), and a and b are empirical parameters, and T is the temperature (K), and P is the pressure (torr) of the atmosphere, and Ps is the pressure (torr) of saturated water vapor at the temperature T, and H (%) is the (relative) humidity. In some embodiments, a is in a range of 170 to 250, and b is in a range of 25 to 75. In some embodiments, a is in a range of 190 to 230, and b is in a range of 40 to 60.

In some embodiments, in order to measure the on-chip temperature of the atmosphere to improve accuracy of the humidity, the MEMS humidity sensor further includes a temperature sensor 160, as shown in FIG. 1. In some embodiments, the temperature sensor 160 is a PN diode, a diode-connected MOS transistor or a thermal resistor. In some embodiments, the temperature sensor 160 shown in FIG. 1 is a thermal resistor. In some embodiments, the temperature sensor 160 is a metal-based thermal resistor.

In some embodiments, the temperature sensor 160 is over or in the second substrate 120, the sensing structure 130 or the first substrate 110. In some embodiments, as shown in FIG. 1, the temperature sensor 160 is in the second substrate 120. In some embodiments, the temperature sensor 160 is in the interconnect and ILD layer 124 of the second substrate 120 and adjacent to the conductive layer 1242. In some embodiments, the temperature sensor 160 is separated from the conductive layer 1242. In some embodiments, the temperature sensor 160 and the conductive layer 1242 belong to a same patterned conductive layer.

In other embodiments, a temperature sensor (not shown) is over the second substrate 120. In other words, the temperature sensor (not shown) over the second substrate 120 can replace the temperature sensor 160 of FIG. 1. In other embodiments, the temperature sensor (not shown) is over the interconnect and ILD layer 124. In other embodiments, the temperature sensor (not shown) is made of inert metal, inert metal alloy, any other suitable material or a combination thereof.

In some embodiments, the MEMS humidity sensor is configured to further measure the pressure of the atmosphere of the second space 120a (i.e., on-chip pressure). In some embodiments, pressure difference between the first space 110a and the second space 120a will result in deformation of the sensing structure 130. The pressure of the atmosphere of the second space 120a can be derived from characteristic parameters (e.g., capacitance or resistance) related to the deformation of the sensing structure 130.

In some embodiments, the MEMS humidity sensor of FIG. 1 is acted as a capacitive type MEMS absolute or differential pressure sensor to reduce chip and package costs and chip dimension. In some embodiments, the pressure of the atmosphere of the second space 120a is obtained through capacitance change of the capacitor constituted by the sensing structure 130, the second space 120a and the conductive layer 1242.

Specifically, for example, each of the first space 110a and the second space 120a has known pressure, and the sensing structure 130 has initial deformation with an initial gap do, which can be called as a correction gap. Subsequently, the second space 120a is communicated with the atmosphere with vapor having the unknown pressure, and the first space 110a still has the same known pressure, and the sensing structure 130 has deformation with a gap d'. Capacitance change=(dielectric constant of the second space $120a$)×(planar area of the sensing structure 130)×($1/d' - 1/d_0$). The unknown pressure of the atmosphere with the vapor of the second space 120a can be calculated through the capacitance change, F=P/A and Hooke's Law.

In other embodiments, a MEMS humidity sensor is acted as a piezo-resistive type MEMS absolute or differential pressure sensor to reduce chip and package costs and chip dimension. In other embodiments, unknown pressure of test atmosphere of a second space is obtained by resistance change of a sensing structure. Specifically, for example, each of a first space and the second space has known pressure, and the sensing structure has initial resistance $R_0$. Subsequently, the second space is communicated with the test atmosphere with vapor having the unknown pressure, and the first space still has the same known pressure, and the sensing structure 130 has resistance R'. Resistance change=$R'-R_0$. The unknown pressure of the test atmosphere with vapor of the second space can be calculated through the resistance change, F=P/A and Hooke's Law.

As mentioned above, in some embodiments, since the on-chip temperature and pressure can be respectively obtained by the temperature sensor 160 and the MEMS humidity sensor, the calculated humidity of the atmosphere of the second space 120a can have high accuracy.

Figure 2:
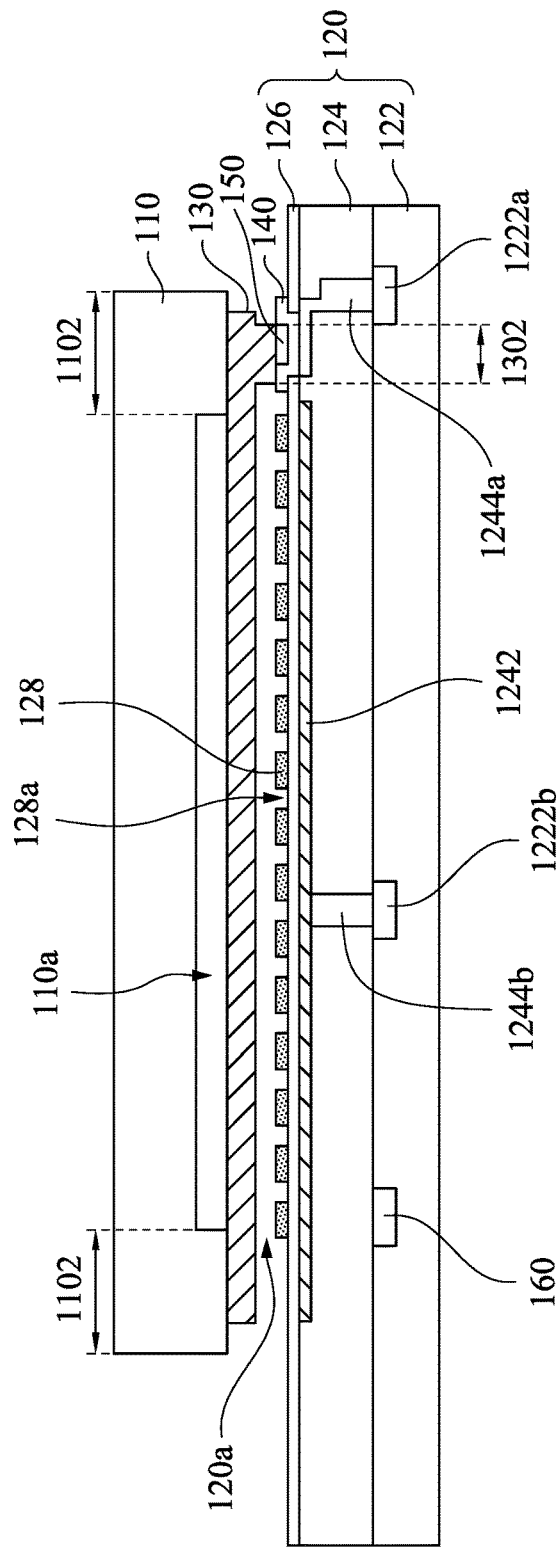
FIG. 2 is a cross-sectional view of a MEMS humidity sensor in accordance with some embodiments of the present disclosure.

FIG. 2 is a cross-sectional view of a MEMS humidity sensor in accordance with some embodiments of the present disclosure. The difference between FIGS. 2 and 1 is that, as shown in FIG. 2, a second substrate 120 includes a polyimide film 128 facing the sensing structure 130. The polyimide film 128 is configured to absorb moisture to increase test sensitivity. Other suitable material able to absorb moisture can replace the polyimide film 128.

In some embodiments, the polyimide film 128 is over the second substrate 120. In some embodiments, the polyimide film 128 is over the conductive layer 1242. In some embodiments, the polyimide film 128 is a patterned polyimide film 128 to increase an area of an exposed surface to absorb more moisture, and thus to further increase test sensitivity. In some embodiments, the patterned polyimide film 128 has a plurality of openings 128a separated from each other. In some embodiments, an insulating layer 126 is between the conductive layer 1242 and the polyimide film 128. In some embodiments, the polyimide film 128 has a planar dimension smaller than or equal to a planar dimension of the sensing structure 130. In other embodiments, a polyimide film is in contact with the conductive layer (not shown) over the second substrate 120.

In some embodiments, the MEMS humidity sensor further includes a temperature sensor 160 in the second substrate 120. In some embodiments, as shown in FIG. 2, the temperature sensor 160 is in a bulk substrate 122 of the second substrate 120. In some embodiments, the temperature sensor 160 is at a top of the bulk substrate 122. In some embodiments, the temperature sensor 160 is a PN diode, a diode-connected MOS transistor or a thermal resistor. In some embodiments, the temperature sensor 160 is a silicon-based temperature sensor.

Figure 3A:
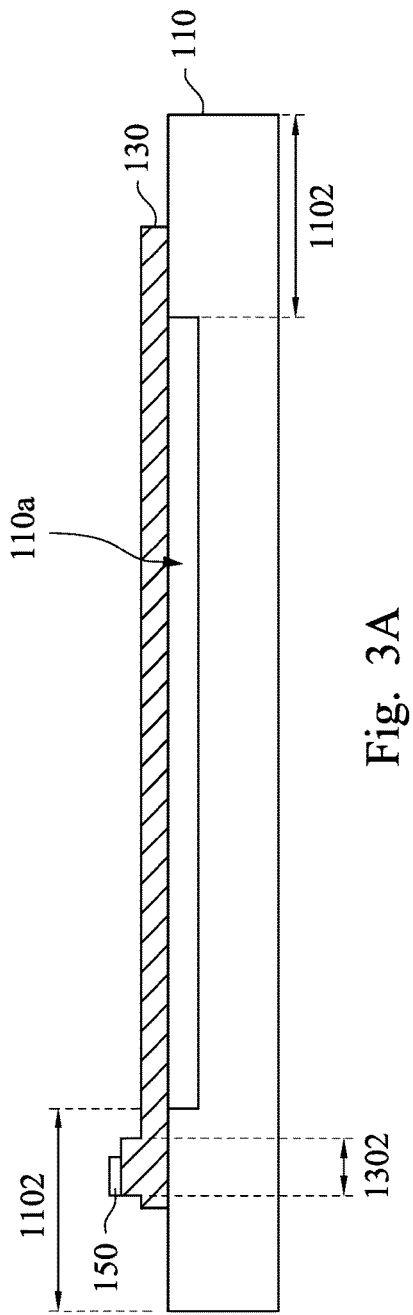
FIGS. 3A to 3C are cross-sectional views at various stages of forming a MEMS humidity sensor of FIG. 2 in accordance with some embodiments of the present disclosure.
Figure 3B:
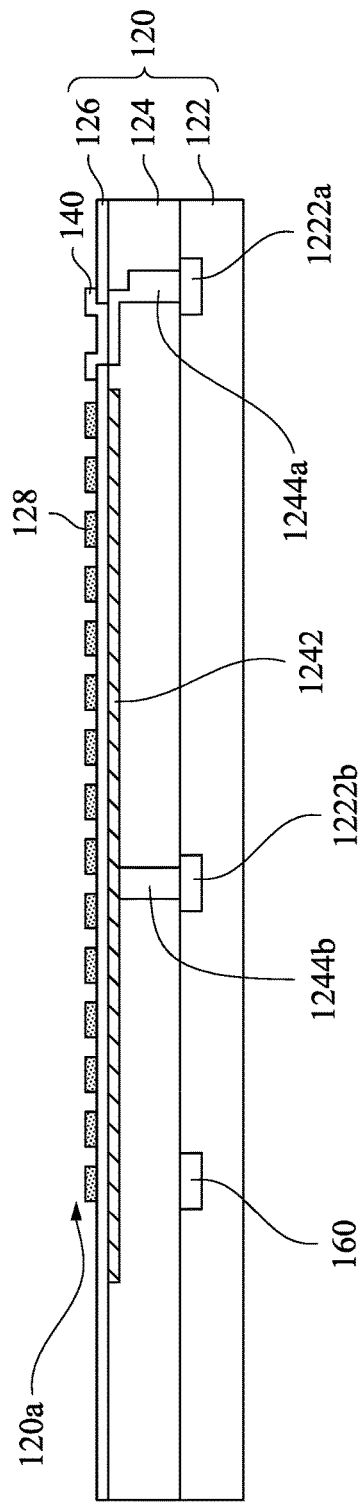
Figure 3C:
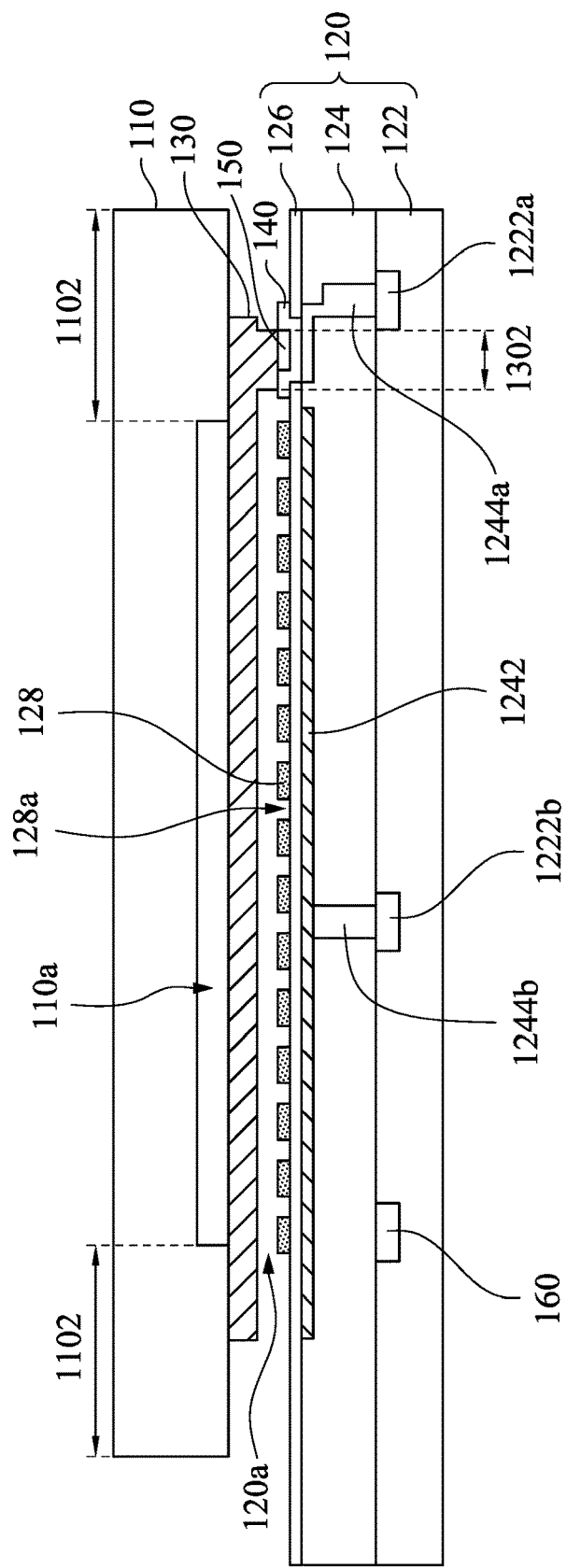

FIGS. 3A to 3C are cross-sectional views at various stages of forming a MEMS humidity sensor of FIG. 2 in accordance with some embodiments of the present disclosure. It is noted that operations of the method described below may be omitted, altered or substituted to manufacture the MEMS humidity sensor of FIG. 1.

In some embodiments, as shown in FIG. 3A, a first substrate 110 is received or provided. In some embodiments, the first substrate 110 is a MEMS substrate. In some embodiments, the first substrate 110 includes a first protruding peripheral portion 1102. In some embodiments, the first protruding peripheral portion 1102 is formed using any patterning processes, such as photolithographic and etching processes, laser drill process or any other suitable processes. In some embodiments, the first protruding peripheral portion 1102 is open shaped (e.g., U shaped) or enclosed shaped (e.g., rectangular or circular shaped) in top view.

In some embodiments, as shown in FIG. 3A, a sensing structure 130 is received or provided. In some embodiments, the sensing structure 130 is made of silicon, metal or a combination thereof. In some embodiments, the sensing structure 130 includes silicon and dopants. In some embodiments, the sensing structure 130 includes a second protruding peripheral portion 1302. In some embodiments, the second protruding peripheral portion 1302 is formed using any patterning processes, such as photolithographic and etching processes, laser drill process or any other suitable processes. In some embodiments, the second protruding peripheral portion 1302 is open shaped (e.g., U shaped) in top view. In some embodiments, a second bonding pad 150 is formed over the sensing structure 130. In some embodiments, the second bonding pad 150 is made of metal, alloy or semiconductor materials.

As shown in FIG. 3A, a portion on a side of the sensing structure 130 is bonded to a portion of the first substrate 110 (e.g., the first protruding peripheral portion 1102) to form a first space 110a between the first substrate 110 and the sensing structure 130. In some embodiments, the portion on the side of the sensing structure 130 is bonded to the portion of the first substrate 110 by a thermal process. In some embodiments, there is silicon bonding between the sensing structure 130 and the portion of the first substrate 110. In some embodiments, the first space 110a is communicated with or isolated from outside.

In some embodiments, as shown in FIG. 3B, a second substrate 120 is received, and the second substrate 120 includes a conductive layer 1242 adjacent to an upper surface of the second substrate 120. In some embodiments, the second substrate 120 includes a bulk substrate 122. In some embodiments, the second substrate 120 includes transistors in the bulk substrate 122, such as a first transistor 1222a and a second transistor 1222b. In some embodiments, the second substrate 120 includes an interconnect and ILD layer 124. In some embodiments, the second substrate 120 includes sensing circuit(s) in the interconnect and ILD layer 124, such as a first sensing circuit 1244a and a second sensing circuit 1244b.

In some embodiments, an insulating layer 126 is formed over the conductive layer 1242. In some embodiments, the insulating layer 126 is made of silicon oxide, silicon nitride, silicon oxynitride, any other suitable material or a combination thereof. In some embodiments, the insulating layer 126 is formed using any suitable deposition technique, such as chemical vapor deposition (CVD) or physical vapor deposition (PVD). In some embodiments, a first bonding pad 140 is formed adjacent to the insulating layer 126.

In some embodiments, a polyimide film 128 is formed over the conductive layer 1242. In some embodiments, the polyimide film 128 is formed over the insulating layer 126. In some embodiments, the polyimide film 128 is formed using any suitable film formation technique, such as coating. In some embodiments, a patterning process, such as photolithographic and etching processes, or laser drill process, is performed on the polyimide film 128 to form a plurality of openings 128a separated from each other.

In some embodiments, as shown in FIGS. 3A to 3C, the first substrate 110 and the sensing structure 130 of FIG. 1 are reversed, and a portion on an opposite side of the sensing structure 130 (e.g., the second protruding peripheral portion 1302) is bonded to a portion of the second substrate 120 to form a second space 120a between the conductive layer 1242 and the sensing structure 130. In some embodiments, the portion on the opposite side of the sensing structure 130 is bonded to the portion of the second substrate 120 by a thermal process. In some embodiments, the second bonding pad 150 is bonded to the first bonding pad 140 by a thermal process. In some embodiments, there is eutectic bonding, such as Ge/Al, Ge/Au or Si/Au, or diffusion bonding, such as Si/Al or Si/Ti, between the second bonding pad 150 and the first bonding pad 140. In some embodiments, the second space 120a is communicated with the atmosphere.

In some embodiments, as shown in FIGS. 3C and 2, another portion of the first substrate 110 is removed. The other portion of the first substrate 110 is not overlapped with the sensing structure 130. Accordingly, in the embodiments, as shown in FIG. 2, the first substrate 110 has a planar dimension (in top view) smaller than a planar dimension (in top view) of the second substrate 120. In some embodiments, the other portion of the first substrate 110 is removed by etching or dicing. In some embodiments, the first substrate 110 has a groove (not shown) for etching or dicing. In some embodiments, the other portion of the first substrate 110 is removed after the portion on the opposite side of the sensing structure 130 is bonded to the portion of the second substrate 120.

According to some embodiments, a MEMS humidity sensor includes a first substrate, a second substrate and a sensing structure. The second substrate is substantially parallel to the first substrate. The sensing structure is between the first substrate and the second substrate, and bonded to a portion of the first substrate and a portion of the second substrate, in which the second substrate includes a conductive layer facing the sensing structure, and a first space between the first substrate and the sensing structure is communicated with or isolated from outside, and a second space between the conductive layer and the sensing structure is communicated with an atmosphere, and the sensing structure, the second space and the conductive layer constitute a capacitor.

According to some embodiments, a MEMS humidity sensor includes a first substrate, a second substrate and a sensing structure. The first substrate includes a first protruding peripheral portion. The second substrate is substantially parallel to the first substrate. The sensing structure is between the first substrate and the second substrate, and bonded to the first protruding peripheral portion of the first substrate, and includes a second protruding peripheral portion bonded to the second substrate, in which the second substrate includes a conductive layer facing the sensing structure, and a first space between the first substrate and the sensing structure is communicated with or isolated from outside, and a second space between the conductive layer and the sensing structure is communicated with an atmosphere, and the sensing structure, the second space and the conductive layer constitute a capacitor.

According to some embodiments, a method of manufacturing a MEMS humidity sensor includes: bonding a portion on a side of a sensing structure to a portion of a first substrate to form a first space between the first substrate and the sensing structure; and bonding a portion on an opposite side of the sensing structure to a portion of the second substrate including a conductive layer to form a second space between the conductive layer and the sensing structure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A micro-electro mechanical system (MEMS) humidity sensor, comprising:
 a first substrate;

a second substrate substantially parallel to the first substrate; and a sensing structure between the first substrate and the second substrate, and bonded to a portion of the first substrate and a portion of the second substrate, wherein the second substrate comprises a conductive layer facing the sensing structure, and a first space between the first substrate and the sensing structure is communicated with or isolated from outside, and a second space between the conductive layer and the sensing structure is communicated with an atmosphere, and the sensing structure, the second space and the conductive layer constitute a capacitor.

2. The MEMS humidity sensor of claim 1, further comprising a temperature sensor configured to measure the temperature.

3. The MEMS humidity sensor of claim 2, wherein the temperature sensor is a PN diode, a diode-connected MOS transistor, or a thermal resistor.

4. The MEMS humidity sensor of claim 2, wherein the temperature sensor is in the second substrate, the sensing structure, or the first substrate.

5. The MEMS humidity sensor of claim 2, wherein the temperature sensor is adjacent to the conductive layer.

6. The MEMS humidity sensor of claim 1, wherein the second substrate comprises a polyimide film that extends therefrom toward the sensing structure.

7. The MEMS humidity sensor of claim 6, wherein the polyimide film is between the conductive layer and the second space.

8. The MEMS humidity sensor of claim 6, wherein the polyimide film has a plurality of openings separated from each other and communicated with the second space.

9. The MEMS humidity sensor of claim 6, wherein the second substrate further comprises an insulating layer between the conductive layer and the polyimide film.

10. The MEMS humidity sensor of claim 1, wherein the second substrate comprises a first sensing circuit and a second sensing circuit respectively coupled to the sensing structure and the conductive layer.

11. The MEMS humidity sensor of claim 1, further comprising:

a first bonding pad over the portion of the second substrate; and a second bonding pad between the sensing structure and the first bonding pad.

12. The MEMS humidity sensor of claim 1, wherein the sensing structure comprises silicon.

13. The MEMS humidity sensor of claim 1, wherein the first space is defined by the first substrate and the sensing structure.

14. The MEMS humidity sensor of claim 1, further comprising an insulating layer over the second substrate, wherein the second space is defined by the insulating layer and the sensing structure.

15. The MEMS humidity sensor of claim 1, further comprising an insulating layer over the second substrate and a polyimide film, wherein the second space is defined by the sensing structure, the insulating layer, and the polyimide film.

16. A MEMS humidity sensor, comprising:

a first substrate comprising a first protruding peripheral portion;

a second substrate substantially parallel to the first substrate; and a sensing structure between the first substrate and the second substrate, and bonded to the first protruding peripheral portion of the first substrate, and comprising a second protruding peripheral portion bonded to the second substrate, wherein the second substrate comprises a conductive layer facing the sensing structure, and a first space between the first substrate and the sensing structure is communicated with or isolated from outside, and a second space between the conductive layer and the sensing structure is communicated with an atmosphere, and the sensing structure, the second space and the conductive layer constitute a capacitor.

17. The MEMS humidity sensor of claim 16, further comprising a temperature sensor over or in the second substrate, the sensing structure, or the first substrate.

18. A method of manufacturing a MEMS humidity sensor, comprising:

bonding a portion on a side of a sensing structure to a portion of a first substrate to form a first space between the first substrate and the sensing structure; and bonding a portion on an opposite side of the sensing structure to a portion of a second substrate comprising a conductive layer to form a second space between the conductive layer and the sensing structure.

19. The method of claim 18, further comprising forming a polyimide film over the conductive layer.

20. The method of claim 19, further comprising forming an insulating layer over the conductive layer before forming the polyimide film over the conductive layer.

* * * * *